United States Patent
Bergmann et al.

(10) Patent No.: US 9,611,505 B2
(45) Date of Patent: Apr. 4, 2017

(54) APPLICATION OF OLIGO-DT MOLECULES TO AVOID GENERATION OF HIGH MOLECULAR PCR PRODUCTS INDUCED BY POLY-A CARRIER

(71) Applicant: Roche Molecular Systems, Inc., Pleasanton, CA (US)

(72) Inventors: Frank Bergmann, Iffeldorf (DE); Stephanie Froehner, Penzberg (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 90 days.

(21) Appl. No.: 14/484,636

(22) Filed: Sep. 12, 2014

(65) Prior Publication Data
US 2015/0079600 A1    Mar. 19, 2015

(30) Foreign Application Priority Data
Sep. 13, 2013 (EP) .................... 13184307

(51) Int. Cl.
*C12P 19/34* (2006.01)
*C12Q 1/68* (2006.01)
*C07H 21/02* (2006.01)

(52) U.S. Cl.
CPC .......... *C12Q 1/6806* (2013.01); *C12Q 1/6848* (2013.01)

(58) Field of Classification Search
CPC ........ C12Q 2521/107; C12Q 2525/173; C12Q 2525/186; C12Q 1/6806; C12Q 1/6848
See application file for complete search history.

(56) References Cited

U.S. PATENT DOCUMENTS

2015/0087027 A1* 3/2015 Makarov ................ C12P 19/34
435/91.3

FOREIGN PATENT DOCUMENTS

WO    WO 2012/054975    * 5/2012

OTHER PUBLICATIONS

Machery-Nagel Gmbh & Co, 2013, "RNA isolation User Manual NucleoSpin RNA XS", Rev. 07:1-37, www.mn-net.com.
Shaw, Kirsty J., et al., 2009, "The use of carrier RNA to enhance DNA extraction from microfluidic-based silica monoliths", Analytica Chimica Acta, 652:231-233.
Vestheim, Hege, et al., 2008, "Blocking primers to enhance PCR amplification of rare sequences in mixed samples—a case study on prey DNA in Antarctic krill stomachs", Frontiers in Zoology, 5(12):1-11.

* cited by examiner

*Primary Examiner* — Teresa Strzelecka
(74) *Attorney, Agent, or Firm* — Carol Johns

(57) ABSTRACT

During RNA isolation carrier nucleic acids such as polyA-RNA are used in order to increase the yield of the isolated RNA. The carrier nucleic acids may lead to high molecular weight products which may interfere in subsequent steps, such as reverse transcription, PCR and gel electrophoresis. The present invention therefore refers to a method and a kit for reverse transcription and the use of a blocking nucleic acid molecule for blocking the carrier polyA-RNA.

8 Claims, 1 Drawing Sheet

APPLICATION OF OLIGO-DT MOLECULES TO AVOID GENERATION OF HIGH MOLECULAR PCR PRODUCTS INDUCED BY POLY-A CARRIER

During RNA isolation carrier nucleic acids such as polyA-RNA are used in order to increase the yield of the isolated RNA. The carrier nucleic acids may lead to high molecular weight products which may interfere in subsequent steps, such as reverse transcription, PCR and gel electrophoresis. The present invention therefore refers to a method and a kit for reverse transcription and the use of a blocking nucleic acid molecule for blocking the carrier polyA-RNA.

The isolation of low amounts of viral RNA out of plasma requires a method which guarantees a low loss rate of RNA which is necessary for further analysis of the viral genome. Viral RNA can be isolated using different methods. One of the most common methods is the manual RNA isolation. For the manual RNA isolation out of plasma which is mostly performed by column based methods a carrier RNA, like polyA, MS2 RNA or tRNA is used to inhibit irreversible binding of the target RNA to the column material. In addition it has been shown that synthetic polyA carrier RNA enhances reversible binding of RNA to the silica surface in the isolation columns which also results in an increased RNA yield (D N. Hengen et al., Trends of Biochemical Sciences 1996, 21, 224-225; M L. Gallagher et al. Biochemical and Biophysical Research Communications 1987, 144, 271-276). The carrier RNA blocks the column material, so that the target RNA can quantitatively be isolated out of the plasma sample. Use of carrier RNA may also have additional beneficial effects such as improvement of target RNA stability (D. Andreasen et al., Methods 2010, 50, S6-S9; R. Kishore et al., J. Forensic. Sci. 2006, 51(5), 1055-1061).

After the isolation a reverse transcription of the RNA is performed to generate cDNA used for the following PCR reaction. Using polyA-RNA as RNA carrier for the isolation step and random hexamers primers for the reverse transcription step, unwanted, unspecific high molecular weight products occur during the PCR reaction which result from the hybridization of polyA-RNA molecules and a portion of random hexamer primers which can bind to polyA-RNA. This high molecular hybridization product is then amplified during PCR which is visible as a high molecular weight (HMW) smear on agarose gels. The generation of the HMW products finally results in a lower amount of amplified target DNA.

The object of the present description is therefore the provision of a method, which does not show the above mentioned drawbacks.

SUMMARY OF THE INVENTION

It was found that the above described HMW products which negatively affect the procedure subsequent to the reverse transcription can be prevented if the polyA-RNA used as a carrier is blocked by oligo-dT molecules which are blocked at the 3'-end.

The present description thus refers to a method of reverse transcription, wherein the method comprises the steps of a) providing a sample comprising RNA, b) contacting the sample with a carrier nucleic acid thereby generating a mixture, c) applying the mixture to a matrix under conditions such that binding of the RNA and the carrier nucleic acid to the matrix occurs, d) separating the matrix with the RNA and the carrier nucleic acid bound to the matrix from the mixture, e) eluting the RNA and the carrier nucleic acid from the matrix thereby generating an eluate, f) adding a blocking nucleic acid to the eluate under conditions such that hybridization of the blocking nucleic acid to the carrier nucleic acid occurs, g) adding a primer to the eluate from step f) under conditions such that hybridization of the primer to the RNA occurs, and h) reverse transcribing the RNA into cDNA.

In a specific embodiment, the carrier nucleic acid is a RNA carrier. In a more specific embodiment, the RNA carrier is polyA-RNA.

In a specific embodiment, the blocking nucleic acid is an oligo-dT molecule. In a more specific embodiment, the oligo-dT molecule is 5'-(dT)n-X-3', wherein (dT)n is a n-mer homo-2'-deoxy-thymidine oligonucleotide, wherein n is 18, 19, 20, 21 or 22, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer. In an even more specific embodiment, n is 20 and X is pC3pC3p. In a specific embodiment, the primer is a random primer. In a more specific embodiment, the random primer is a random hexamer primer.

In a specific embodiment, the matrix comprises a glass fiber fleece.

In a specific embodiment, the sample is selected from the group consisting of serum, blood, plasma, tears, cell culture supernatant, urine and breast milk, saliva, cerebrospinal fluid and sperm.

The present description further refers to the use of a blocking nucleic acid molecule for blocking carrier polyA-RNA during reverse transcription, wherein the blocking nucleic acid molecule is 5'-(dT)n-X-3', wherein (dT)n is a n-mer homo-2'-deoxy-thymidine oligonucleotide, wherein n is 18, 19, 20, 21 or 22, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer. In a specific embodiment, n is 20 and X is pC3pC3p.

The present description further refers to a kit for performing reverse transcription, the kit comprising a) polyA-RNA as a carrier, and b) a blocking nucleic acid as described above.

DETAILED DESCRIPTION OF THE INVENTION

Figure 1:
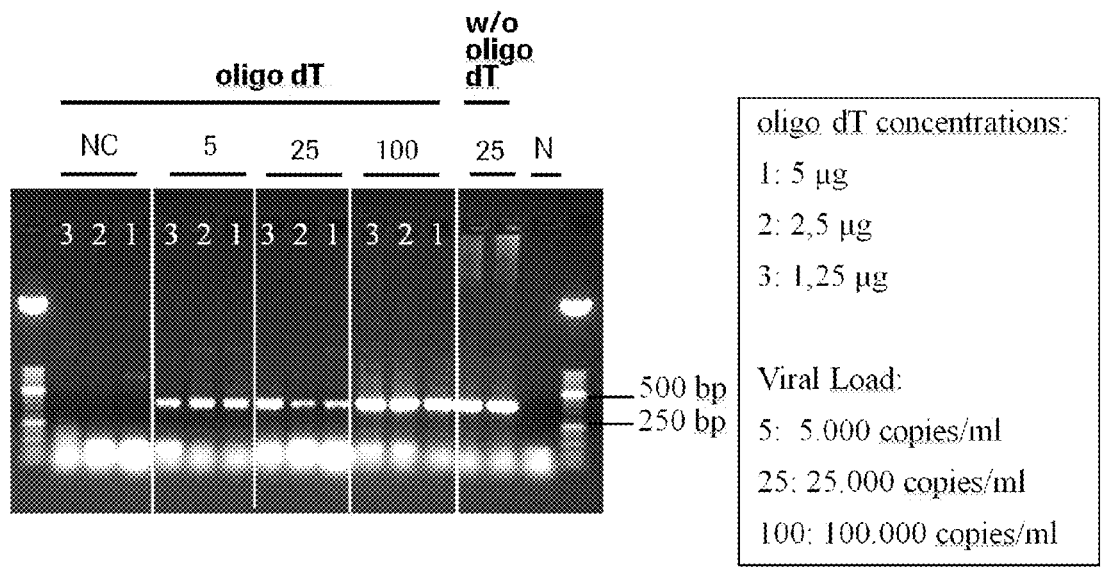
FIG. 1: The Figure shows the comparison of PCR products using an HCV specific primer set for HCV genotype 1a with and without oligo-dT pretreatment before reverse transcription. Different concentrations of oligo-dT and different concentrations of HCV cDNA are compared.

The following definitions are set forth to illustrate and define the meaning and scope of various terms used herein.

The terms "a", "an" and "the" generally include plural referents, unless the context clearly indicates otherwise.

The term "about" as used herein in conjunction with a numerical value modifies that value by extending the boundaries above and below the values. In general, the term "about" modifies a numerical value above and below the stated value by a variance of 5% higher or lower. For example a value of "about 100" means a range of "95 to 105".

The term "amplification" generally refers to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to: standard PCR, long PCR, hot start PCR, qPCR, RT-PCR and Isothermal Amplification.

The term "3'-blocked primer" is used herein as known to the expert in the art and refers to oligonucleotides which are modified at their terminal 3'-hydroxyl group by a blocking group which is able to prevent primer extension by a polymerase reaction. Suited blocking groups are in particular any groups which do not contain a 2'-deoxyribose moiety. Such blocking groups are for example but are not limited to phosphate, substituted phosphate like alkyl or aryl substituted phosphate, ether groups like alkyl ether such as methyl, ethyl or benzyl, 3'-deoxyribose derivatives like 2',3'-dideoxynucleosides or any other hydroxyl protecting group which is stable under amplification conditions like esters such as benzoate or nitrate. Substituted phosphates can be multiply incorporated at the 3'-terminal hydroxyl group by using diols such as alkane diols like 1,3-propanediol (herein referred to as C3-spacer or C3). For ease of synthesis of such 3'-phosphate or substituted phosphate blocked primers use of commercially available 3'-phosphate-CPG or 3'-spacer C3 CPG or 3'-phosphate-CPG together with spacer C3 phosphoramidite (Glen Research Corporation, Sterling, Va.) may be used. In particular suited is a 3'-hydroxyl modification such as phosphate (p), phosphate—1,3-propanediol (pC3), phosphate—1,3-propanediol—phosphate (pC3p), phosphate—1,3-propanediol—phosphate—1,3-propanediol (pC3pC3) or phosphate—1,3-propanediol—phosphate—1,3-propanediol—phosphate (pC3pC3p). The term "carrier nucleic acid" is used herein as known to the expert skilled in the art and refers to different types of RNA, such as polyA-RNA, tRNA and MS2 RNA. Usually such different carrier RNAs origin from bacteriophages. Carrier nucleic acid is used to increase recovery of low amounts of target nucleic acids, such as target RNA, during nucleic acid isolation procedure. Such isolation means the separation of the target nucleic acid from a sample, e.g. by using a solid phase. In general, carrier nucleic acid is added to the sample comprising the target nucleic acid in a large amount. The amount of the carrier nucleic acid is disproportional larger as compared to the target nucleic acid. The carrier nucleic acid and the target nucleic acid compete for example for degeneration processes (enzymatic, physical, chemical), thereby protecting the target nucleic acid. Due to the large amount of the carrier nucleic acid, it is proportionally affected stronger by such processes as compared to the target nucleic acid. As a consequence, the target nucleic acid is affected to a much lower extent, thereby increasing the yield of the target nucleic acid. Carrier nucleic acid is well known in the art and commercially available.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids. While the invention is not limited to a particular set of hybridization conditions, stringent hybridization conditions are preferably employed. Stringent hybridization conditions are sequence-dependent and will differ with varying environmental parameters (e.g., salt concentrations, and presence of organics). Generally, "stringent" conditions are selected to be about 5° C. to 20° C. lower than the thermal melting point (Tm) for the specific nucleic acid sequence at a defined ionic strength and pH. Preferably, stringent conditions are about 5° C. to 10° C. lower than the thermal melting point for a specific nucleic acid bound to a complementary nucleic acid. The Tm is the temperature (under defined ionic strength and pH) at which 50% of a nucleic acid (e.g., tag nucleic acid) hybridizes to a perfectly matched probe.

The term "matrix" as used herein, refers to a surface to which nucleic acids specifically bind while contaminating substances do not. More specifically, the matrix is a silica surface of the glass fiber fleece which can be included in nucleic acid isolation columns. By contacting a sample comprising nucleic acids to such matrix, the nucleic acids bind to the surface of the glass fiber fleece in the presence of a chaotropic salt. This allows the matrix to specifically immobilize nucleic acids. In order to bind RNA to the matrix, the binding conditions can be optimized accordingly to ensure increased immobilization of RNA. Isolation of nucleic acids is performed by specifically binding the nucleic acids to the glass fiber fleece, while contaminating substances (such as salts, proteins and other tissue contaminants) do not bind thereto. In order to remove DNA from the matrix, the nucleic acids bound to the matrix can be digested with DNase directly thereon. After removing the digested DNA fragments and other contaminating substances (e.g. by washing), the remaining isolated RNA can subsequently be eluted in a small volume of water or low-salt buffer.

The term "nucleic acid" generally refers to DNA or RNA, whether it is a product of amplification, synthetically created, products of reverse transcription of RNA or naturally occurring. Typically, nucleic acids are single- or double-stranded molecules and are composed of naturally occurring nucleotides. Double-stranded nucleic acid molecules can have 3' or 5' overhangs and as such are not required or assumed to be completely double-stranded over their entire length. Furthermore, the term nucleic acid can be composed of non-naturally occurring nucleotides and/or modifications to naturally occurring nucleotides. Examples are listed herein, but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorophores and quenchers; phosphorothioate, methylphosphonates, phosphoramidates and phosphotriester linkages between nucleotides to prevent degradation; methylation; and modified bases or nucleotides such as 2'-deoxyinosine, 5-bromo-2'-deoxyuridine, 2'-deoxyuridine, 2-aminopurine, 2',3'-dideoxycytidine, 5-methyl-2'-deoxycytidine, locked nucleic acids (LNA's), iso-dC and—dG bases, 2'O-methyl RNA bases and fluorine modified bases.

As used herein, the term "oligo-dT" or "oligo-dT molecule" refers to a homopolymer consisting exclusively of thymidines. Preferred length of the oligo-dT molecule is 10 to 100 bases, more preferred is a length of 10 to 30 bases, most preferred is a length of 20 bases. The oligo-dT molecule is preferably blocked at its 3'-hydroxyl group by a blocking group to prevent extension by a polymerase reaction. It is known to the expert in the art that oligo-dT molecules can also be modified as long as the molecule is still capable of hybridizing to polyA-RNA. Modifications are but not limited to all types of thymidine analogs like 2'-deoxyuridine, 2'-O-methyl-uridine, LNA (locked nucleic acid) thymidine or uridine derivatives, PNA (peptide nucleic acid) thymine or uracil derivatives, HNA (hexitol nucleic acid) thymidine or uridine derivatives or base modified uracil derivatives like 5-propinyl-uracil, but also modification with labels like fluorescent labels or haptens or modification with nucleotides or nucleotide sequences other than thymidine and uridine.

As used herein, the term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. The term oligonucleotide may also be used interchangeably with the term "polynucleotide." The term "polymerase chain reaction" (or "PCR") refers to a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. With PCR, it is possible to amplify a single copy of a specific target sequence in genomic DNA to a level detectable by several different methodologies known to those skilled in the art. In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. Ligation mediated PCR refers to PCR that is performed, wherein the primers are homologous (e.g., complementary) to linkers that are ligated to the ends of DNA (e.g., DNA fragments).

The term "qPCR" generally refers to the PCR technique known as real-time quantitative polymerase chain reaction, quantitative polymerase chain reaction or kinetic polymerase chain reaction. This technique simultaneously amplifies and quantifies target nucleic acids using PCR wherein the quantification is by virtue of an intercalating fluorescent dye or sequence-specific probes which contain fluorescent reporter molecules that are only detectable once hybridized to a target nucleic acid.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "random hexamer primer" refers to oligonucleotide sequences of a length of 6 bases which are synthesized entirely randomly by using a mixture of the four bases A, G, C and T at every coupling step to give a numerous range of all possible 6-mer sequences (4096 sequences) that have the potential to anneal to a plurality of complementary sequences on a nucleic acid sequence and act as a primer to commence first strand cDNA synthesis. The term "RNA" is used herein as known to the expert skilled in the art and refers to pre-mRNA, pre-mRNA transcripts, mRNA, transcript processing intermediates, miRNA, non-coding RNA, mature mRNA used for translation and transcripts from a gene or genes, or nucleic acids derived therefrom. Transcript processing includes processes such as splicing, editing, modifying and degrading. mRNA including samples include, but are not limited to mRNA, mRNA transcripts of the gene or genes, cDNA originating from mRNA using reverse transcription, RNA transcribed from amplified DNA, cRNA transcribed from cDNA, DNA amplified from the genes, and the like. Furthermore, within the scope of the description, the term "RNA" may also refer to tRNA, rRNA, miRNA and carrier RNA.

As used herein, the term "sample" is used in its broadest sense. In one sense, it is meant to include a nucleic acid specimen obtained from any source. Biological nucleic acid samples may be obtained from animals (including humans) and encompass nucleic acids isolated from fluids, solids, tissues, etc. Biological nucleic acid sample may also come from non-human animals, including, but not limited to, vertebrates such as rodents, non-human primates, ovines, bovines, ruminants, lagomorphs, porcines, caprines, equines, canines, felines, ayes, etc. Biological nucleic acids may also be obtained from prokaryotes, like bacteria and other non-animal eukaryotes such as plants. It is contemplated that the present invention is not limited by the source of nucleic acids sample, and any nucleic acid from any biological kingdom fmds utility in methods as described herein.

If RNA is isolated from a complex sample by a matrix, carrier nucleic acids are usually used to increase the yield of isolated RNA. Such increase is essential, especially if the RNA of interest is contained in the complex sample in very low amounts, e.g. viral RNA in plasma. Such increase in yield increases the chance of success in subsequent procedures, such as reverse transcription followed by PCR. If polyA-RNA is used as carrier nucleic acid for the isolation step and in addition if random hexamers are used for the reverse transcription step, unwanted, unspecific high molecular weight (HMW) products occur during the PCR reaction. Such HMW products result from the hybridization of polyA-RNA molecules to a portion of the random hexamer primers thereby leading to a sequence of multiple elements of polyA-RNA molecules and random hexamer primers. Such HMW products are amplified during PCR which appear as a smear in the HMW range on agarose gels. The generation of the HMW products finally results in a lower amount of amplified target DNA.

The object of the present description was therefore the prevention of the occurrence of the above explained BMW products when using polyA-RNA and random hexamer primers for cDNA generation by reverse transcription. Therefore, oligo-dT molecules have been synthesized which are able to hybridize to the polyA-RNA and are capable to block the molecules in order to avoid their hybridization to the random hexamers and the generation of HMW products. To ensure that the oligo-dT molecules do not lead to the elongation of the 3' end of the oligo-dT molecules, the oligo-dT molecules comprise a blocking group.

One aspect of the present description is a method of reverse transcription, wherein the method comprises the steps of a) providing a sample comprising RNA, b) contacting the sample with a carrier nucleic acid thereby generating a mixture, c) applying the mixture to a matrix under conditions such that binding of the RNA and the carrier nucleic acid to the matrix occurs, d) separating the matrix with the RNA and the carrier nucleic acid bound to the matrix from the mixture, e) eluting the RNA and the carrier nucleic acid from the matrix thereby generating an eluate, f) adding a blocking nucleic acid to the eluate under conditions such that hybridization of the blocking nucleic acid to the carrier nucleic acid occurs, g) adding a primer to the eluate from step f) under conditions such that hybridization of the primer to the RNA occurs, and h) reverse transcribing the RNA into cDNA.

In a specific embodiment, the carrier nucleic acid is an RNA carrier. In a more specific embodiment, the RNA carrier is selected from the group consisting of polyA-RNA, tRNA and MS2 RNA. In a more specific embodiment, the RNA carrier is polyA-RNA. In an even more specific embodiment, the polyA-RNA originates from a bacteriophage. As described above in detail, the carrier nucleic acid is used to increase recovery of low amounts of target nucleic acids, such as target RNA, during nucleic acid isolation procedure. PolyA-RNA has a molecular weight of about 100 to about 500 kDa and consists of a series of adenosine nucleotides. In a specific embodiment, the blocking nucleic acid is an oligo-dT molecule. In a more specific embodiment, the oligo-dT molecule comprises from 10 to 30 nucleotides. In an even more specific embodiment, the oligo-dT molecule comprises from 15 to 25 nucleotides. In an even more specific embodiment, the oligo-dT molecule comprises from 18 to 22 nucleotides. In an even more specific embodiment, the oligo-dT molecule comprises 20 nucleotides. In a specific embodiment, the oligo-dT molecule is blocked at the 3'-end. In a more specific embodiment, the oligo-dT molecule is blocked at the 3'-hydroxyl group by a substituted phosphate. In an even more specific embodiment, the substituted phosphate comprises C3. In an even more specific embodiment, C3 is a 1,3-propanediol spacer.

In a specific embodiment, the oligo-dT molecule is 5'-(dT)n-X-3', wherein (dT)n is a n-mer homo-2'-deoxy-thymidine oligonucleotide, wherein n is 10, 11, 12, 13, 14, 15, 16, 17, 18, 19, 20, 21, 22, 23, 24, 25, 26, 27, 28, 29 or 30, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer. In a more specific embodiment, the oligo-dT molecule is 5'-(dT)n-X-3', wherein (dT)n is a n-mer homo-2'-deoxy-thymidine oligonucleotide, wherein n is 18, 19, 20, 21 or 22, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer. In a preferred embodiment, n is 20 and X is pC3pC3p.

In a more specific embodiment, the oligo-dT molecule is 5'-(dT)20-X-3', wherein (dT)20 is a 20-mer homo-2'-deoxy-thymidine oligonucleotide, wherein X is selected from the group consisting of p, pC3, pC3p, pC3pC3 and pC3pC3p, and wherein X is bound to the 3'-terminal 0hydroxyl group of (dT)20 and wherein p is a phosphate and C3 is a 1,3-propanediol spacer. In a preferred embodiment, X is pC3pC3p.

Thus, in the preferred embodiment, the oligo-dT molecule is 5'-(dT)20-pC3pC3p-3', wherein (dT)20 is a 20-mer homo-2'-deoxy-thymidine oligonucleotide, and wherein p is a phosphate and C3 is a 1,3-propanediol spacer.

In a specific embodiment, the primer is a random primer. In a more specific embodiment, the random primer comprises 5 to 7 nucleotides. In a more specific embodiment, the random primer comprises 6 nucleotides, i.e. the random primer is a random hexamer primer. The random hexamer primers are synthesized entirely randomly by using a mixture of A, G, C and T at every coupling step to give a numerous range of all possible 6-mer sequences (4096 sequences). The resulting plurality of random hexamer primers anneals at a plurality of random sequences on a nucleic acid sequence and act as primers to commence first strand cDNA synthesis.

In a specific embodiment, the matrix comprises a silica surface. In a specific embodiment the matrix comprises a silica surface of a glass fiber fleece. In a more specific embodiment the matrix comprises a glass fiber fleece. The sample comprising nucleic acids is contacted with such matrix, wherein the nucleic acids bind to the silica surface of the glass fiber fleece. Binding of RNA to the matrix can be increased by optimizing the binding conditions accordingly. Contaminating substances do not bind to the matrix and may be removed by washing. In a specific embodiment, the sample is obtained from a first organism. In a more specific embodiment, the first organism is an animal, such as a human. In a specific embodiment, the sample is obtained from animals. In a more specific embodiment, the sample is obtained from humans. In an even more specific embodiment, the sample is selected from the group consisting of serum, blood, plasma, tears, cell culture supernatant, urine and breast milk, saliva, cerebrospinal fluid and sperm.

In a specific embodiment, the RNA originates from a second organism. In a more specific embodiment, the second organism is a virus. In an even more specific embodiment, the second organism is a Hepatitis C virus (HCV). In a specific embodiment, the RNA is viral RNA. In a more specific embodiment, the RNA is the RNA from HCV. In a specific embodiment, the sample from the first organism comprises the RNA from the second organisms. In a more specific embodiment, the sample is selected from the group consisting of serum, blood, plasma, tears, cell culture supernatant, urine and breast milk, saliva, cerebrospinal fluid and sperm. In an even more specific embodiment, the sample is plasma. In a more specific embodiment, the human plasma comprises RNA from HCV.

Another aspect of the present description is the use of a blocking nucleic acid molecule for blocking the carrier polyA-RNA, wherein the blocking nucleic acid molecule is 5'-(dT)n-X-3', wherein (dT)n is a n-mer homo-2'-deoxythymidine oligonucleotide, wherein n is 10, 11, 12, 13, 14, 15, 16, 17, 18, 19, 20, 21, 22, 23, 24, 25, 26, 27, 28, 29 or 30, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer.

In a more specific embodiment, the oligo-dT molecule is 5'-(dT)n-X-3', wherein (dT)n is a n-mer homo-2'-deoxythymidine oligonucleotide, wherein n is 18, 19, 20, 21 or 22, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer. In a preferred embodiment, n is 20 and X is pC3pC3p.

In an even more specific embodiment, the blocking nucleic acid molecule is 5'-(dT)20-X-3', wherein (dT)20 is a 20-mer homo-2'-deoxy-thymidine oligonucleotide, wherein X is selected from the group consisting of p, pC3, pC3p, pC3pC3 and pC3pC3p, and wherein X is bound to the 3'-terminal hydroxyl group of (dT)20 and wherein p is a phosphate and C3 is a 1,3-propanediol spacer. In a preferred embodiment, X is pC3pC3p.

Thus, in the preferred embodiment, the oligo-dT molecule is 5'-(dT)20-pC3pC3p-3', wherein (dT)20 is a 20-mer homo-2'-deoxy-thymidine oligonucleotide, and wherein p is a phosphate and C3 is a 1,3-propanediol spacer.

Another aspect of the present description is a kit for performing reverse transcription, the kit comprising a) polyA-RNA as a carrier, and b) a blocking nucleic acid as described herein. In a specific embodiment, the blocking nucleic acid is an oligo-dT molecule. In a more specific embodiment, the oligo-dT molecule comprises from 10 to 30 nucleotides. In an even more specific embodiment, the oligo-dT molecule comprises from 15 to 25 nucleotides. In an even more specific embodiment, the oligo-dT molecule comprises from 18 to 22 nucleotides. In an even more specific embodiment, the oligo-dT molecule comprises 20 nucleotides. In a specific embodiment, the oligo-dT molecule is blocked at the 3'-end. In a more specific embodiment, the oligo-dT molecule is blocked at the 3'-hydroxyl group by a substituted phosphate. In an even more specific embodiment, the substituted phosphate comprises C3. In an even more specific embodiment, C3 is a 1,3-propanediol spacer.

In a specific embodiment, the oligo-dT molecule is 5'-(dT)n-X-3', wherein (dT)n is a n-mer homo-2'-deoxy-thymidine oligonucleotide, wherein n is 10, 11, 12, 13, 14, 15, 16, 17, 18, 19, 20, 21, 22, 23, 24, 25, 26, 27, 28, 29 or 30, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer. In a more specific embodiment, the oligo-dT molecule is 5'-(dT)n-X-3', wherein (dT)n is a n-mer homo-2'-deoxy-thymidine oligonucleotide, wherein n is 18, 19, 20, 21 or 22, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer. In a preferred embodiment, n is 20 and X is pC3pC3p.

In a more specific embodiment, the oligo-dT molecule is 5'-(dT)20-X-3', wherein (dT)20 is a 20-mer homo-2'-deoxy-thymidine oligonucleotide, wherein X is selected from the group consisting of p, pC3, pC3p, pC3pC3 and pC3pC3p, and wherein X is bound to the 3'-terminal hydroxyl group of (dT)20 and wherein p is a phosphate and C3 is a 1,3-propanediol spacer. In a preferred embodiment, X is pC3pC3p.

Thus, in the preferred embodiment, the oligo-dT molecule is 5'-(dT)20-pC3pC3p-3', wherein (dT)20 is a 20-mer homo-2'-deoxy-thymidine oligonucleotide, and wherein p is a phosphate and C3 is a 1,3-propanediol spacer.

The following examples 1 to 6 are provided to aid the understanding of the present invention, the true scope of which is set forth in the appended claims. It is understood that modifications can be made in the procedures set forth without departing from the spirit of the invention.

EXAMPLE 1

Preparation of Virus Dilutions

A Hepatitis C virus (HCV) positive sample with a defined number of HCV virus copies (EDTA plasma GT1A, Trina, Cat. No. DH1302, Lot 13BDH 28725, HCV: 876487 IU/ml=2,364×10e6 copies/ml) was used to prepare HCV samples containing viral loads of 5,000, 25,000 and 100,000 copies/ml. For dilution of the HCV positive sample HCV negative plasma material was used (Plasma-K3EDTA Hum. Pool PCR-NEG, Roche Diagnostics GmbH, Mat.: 03357163001, Lot: 10942000). The HCV positive plasma as well as the HCV negative plasma material was thawed and centrifuged for 10 min at 1,898×g to separate solid impurities which might inhibit subsequent PCR. After the centrifugation step the dilutions were prepared.

EXAMPLE 2

RNA Isolation

The virus RNA is isolated using the High Pure Viral Nucleic Acid Large Volume Kit (Roche Diagnostics GmbH, Mat.: 05114403001). The kit's principle is based on the spin column technology. The virus is lysed within a buffer containing the chaotropic salt guanidine hydrochloride, a non-ionic surfactant and proteinase K. The released nucleic acids are disrupted in their structure in presence of the chaotropic salt. Thus, they can bind to the glass fiber fleece which is integrated in the spin column. The bound nucleic acids are purified from PCR inhibitors, proteins, salts and other compounds. Subsequently, they are eluted with water which restores their structure. The kit is applied with polyA-RNA as carrier for increased recovery of nucleic acids.

The RNA isolation was performed according to the manufacturer's instructions. 1 ml of the diluted HCV positive plasma samples were added to a 15 ml tube. 1 ml of binding buffer supplemented with 15 µl of polyA-RNA and 250 µl of proteinase K was added and incubated for 15 min at 70° C. Subsequently, 400 µl of binding buffer were added and mixed. Next the samples were transferred to the High Pure Extender Assembly. Therefore, the entire sample was pipetted into the upper reservoir of the High Pure Extender Assembly. The entire High Pure Filter Tube assembly was then inserted into a standard table-top centrifuge with a swing-bucket rotor and was centrifuged 5 min at 4,000×g. After centrifugation the Filter Tube was removed from the High Pure Extender Assembly and the flow-through was discarded. The Filter Tube was combined with a new Collection Tube and 500 µl of Inhibitor Removal Buffer was added to the upper reservoir of the Filter Tube and was centrifuged 1 min at 8,000×g. After centrifugation the Filter Tube was removed from the Collection Tube and the Filter Tube was combined with a new Collection Tube. The flow through was again discarded. After that 450 µl of Wash buffer was added to the upper reservoir of the Filter Tube and was centrifuged 1 min at 8,000×g and the flow through was discarded again. This washing step was repeated. After that the Filter Tube Collection Tube assembly was left in the centrifuge and centrifuged for 30 sec at maximum speed to remove any residual Wash buffer. The Collection Tube was discarded and the Filter Tube was inserted in a nuclease-free, sterile 1.5 ml micro centrifuge tube. The viral RNA was eluted using 50 µl of Elution buffer to the upper reservoir of the Filter Tube incubated for 1 min at room temperature and the tube assembly was then centrifuged 1 min at 8,000×g. After RNA isolation, extracted RNA is concentrated to obtain a smaller volume for the following steps. For this approach the Agencourt Ampure RNA Clean XP Beads (Beckman Coulter) were used. The magnetic beads bind nucleic acids, and by placing the plate on the SPRI Plate 96 Super Magnet Plate (Beckman Coulter) the beads were separated from the solution. In this way contaminants were washed away, and nucleic acids were eluted afterwards from the beads.

The RNA concentration was determined according to the manufacturer's instructions.

EXAMPLE 3

Synthesis of 5'-(dT)20-pC3pC3p-3'

Blocking oligonucleotide 5'-(dT)20-pC3pC3p-3' was synthesized in a 1 µmole scale synthesis on an ABI 394 DNA synthesizer using standard automated solid phase DNA synthesis procedure and applying phosphoramidite chemistry. 3'-Phosphate CPG (Glen Research, cat. no. 20-2900-41) and dT phosphoramidite (Sigma Aldrich, cat. no. T111031) as well as Spacer phosphoramidite C3 (Glen Research, cat. no. 10-1913) were used as building blocks. Both phosphoramidites were applied at a concentration of 0.1 M in DNA grade acetonitrile. Standard DNA cycles and reagents were used for the assembly of the oligonucleotide. Then, a standard cleavage program was applied for the cleavage of the 5'-DMT protected oligonucleotide from the support by conc. ammonia. Residual protecting groups were cleaved by treatment with conc. ammonia (4 h at 56° C.). Crude DMT protected oligonucleotide was evaporated and purified by RP HPLC (column: PRP1 (Hamilton part no. 79352)) using a 0.1 M triethylammonium acetate pH 7/acetonitrile gradient. Product fractions were combined and desalted by dialysis (MWCO 1000, SpectraPor 6, part no. 132638) against water for 3 days, thereby also cleaving DMT group. Finally, the oligonucleotide was lyophilized.
Yield: 360 nmoles.

EXAMPLE 4

Blocking of Carrier RNA

To prevent the generation of high molecular weight products 5 µg, 2.5 µg and 1.25 µg of oligo-dT (5'-(dT)20-pC3pC3p-3') were added to the isolated RNA. Different HCV viral load plasma samples with the following concentrations were used: 5,000 copies/ml; 25,000 copies/ml; 50,000 copies/ml (see FIG. 1).

To prevent the generation of high molecular weight products 2.5 µg, 1.25 µg and 0.625 µg of oligo-dT were added to the isolated RNA. HCV viral load plasma samples concentration was 5,000 copies/ml (see FIG. 2).

EXAMPLE 5

Reverse Transcription

Prior to the reverse transcription different amounts of oligo-dT were added to the concentrated RNA sample as described in Example 4. Reverse transcription was then performed using the Transcriptor First Strand cDNA Synthesis Kit (Roche Diagnostics GmbH, Mat.: 0489703001) in combination with random hexamer primers (RH) for priming. 13.5 µl of sample was mixed with 4 µl of 400 µM RH followed by a denaturation step for 10 min at 65° C. After that the sample was put on ice immediately and 8 µl of the reagent master mix was added. Per reaction the master mix consisted of 5 µl Transcriptase Reaction Buffer (5×), 0.5 µl RNase Inhibitor (40 U/µl), 2 µl dNTP mix (10 mM each) and 0.5 µl Reverse Transcriptase (40 U/µl). The reaction was incubated for 25 min at 25° C. (incubation step), followed by 60 min at 50° C. (reverse transcription) and finalized by 5 min at 85° C. (inactivation of Reverse Transcriptase). Afterwards 1 ml RNase (1 U/ml) was added with a subsequent incubation for 20 min at 37° C. The generated cDNA was used as a template for the following PCR reactions.

EXAMPLE 6

PCR

An HCV specific primer set for HCV genotype 1a was used for amplification. For the amplicon PCR the Fast Start High Fidelity PCR System (Roche Diagnostics GmbH, Mat.: 04738284001) and the PCR Nucleotide Mix (Roche Diagnostics GmbH, Mat.: 11581495001) were used. The master mix was composed of 12.75 µl H$_2$O (PCR grade), 2.5 µl 10× Fast Start PCR Reaction Buffer (incl. 18 mM MgCl$_2$), 1 µl DMSO, 1 µl dNTP (10 mM each) and 0.75 µl Fast Start High Fidelity Enzyme (5 U/µl). 2 µl of forward and reverse primer (10 mM each) and 3 µl of cDNA were added. The plate was sealed, shortly centrifuged and incubated as depicted in table 1 (amplification program).

| Step | Temperature in ° C. | Time | Number of Cycles |
|---|---|---|---|
| Denaturation | 95 | 3 min | 1 |
| Amplification | 95 | 30 s | 45 |
|  | 50 | 30 s |  |
|  | 72 | 50 s |  |
| Elongation | 72 | 8 min | 1 |

EXAMPLE 7

Gelelectrophoresis

To analyze the generated PCR products a gel electrophoresis with a 1% agarose gel was performed. Therefore, 1% agarose was solved in 1×TBE (Tris-Borat-EDTA) buffer. The solution was heated until all agarose crystals were dissolved. 0.06 µl of ethidium bromide per 1 ml of 1×TBE buffer was added carefully to the cooled solution. Subsequently, the agarose solution was cast in the desired gel cassette. Before loading the samples, one part of 10×Blue Juice Loading Buffer (Invitrogen, Mat.: 10816015) was applied to four parts of the samples. Additionally, 6 µl of DNA Molecular Weight Marker XIII 50 base pair ladder (Roche Diagnostics GmbH, Mat.: 11721925001) was filled in another gel pocket. Electrophoresis was performed at 120 V for 35 min and DNA bands were visualized afterward using an UV light box. Agarose gels were loaded as follows.

The agarose gel depicted in FIG. 1 was loaded as follows: Right lane: 6 µl Molecular Weight Marker. N: control, water control w/o reagent mix. With oligo-dT: NC: negative control, lanes NC 1, NC 2, NC 3—no sample material included, HCV specific primers were added to the PCR reagent mix, instead of HCV cDNA water was substituted; different pretreatment concentrations of oligo-dT were added to the negative controls; NC 3=1.25 µg oligo-dT, NC 2=2.5 µg oligo-dT, NC 1=5 µg oligo-dT. Oligo-dT sample 5: HCV sample—5,000 copies/ml: HCV cDNA with a concentration of 5,000 copies/ml was amplified with oligo-dT pretreatment before reverse transcription at different concentrations of oligo-dT lane 5-3=1.25 µg oligo-dT, lane 5-2=2.5 µg oligo-dT, lane 5-3=5 µg oligo-dT. Oligo-dT sample 25: HCV sample 25,000 copies/ml: HCV cDNA with a concentration of 25,000 copies/ml was amplified with oligo-dT pretreatment before reverse transcription at different concentrations of oligo-dT, lane 5-3=1.25 µg oligo-dT, lane 5-2=2.5 µg oligo-dT, lane 5-3=5 µg oligo-dT. Oligo-dT sample 100: HCV sample 100,000 copies/ml: HCV cDNA with a concentration of 100,000 copies/ml is amplified with oligo-dT pretreatment before reverse transcription at different concentrations of oligo-dT, lane 5-3=1.25 µg oligo-dT, lane 5-2=2.5 µg oligo-dT, lane 5-3=5 µg oligo-dT. Without (w/o) oligo-dT: Sample 25: HCV sample 25,000 copies/ml: HCV cDNA with a concentration of 25,000 copies/ml was amplified without oligo-dT pretreatment before reverse transcription. The agarose gel depicted in FIG. 2 was loaded as follows: Right lane: 6µl Molecular Weight Marker. N: control, water control w/o reagent mix. With oligo-dT:NC: Negative control (no sample material included), HCV specific primers were added to the PCR reagent mix, instead of HCV cDNA water was substituted, oligo-dT pretreatment at a concentration of 0.625 µg oligo-dT. Oligo-dT sample 0.625 µg: HCV cDNA sample with a concentration of 5,000 copies/ml was amplified with 0.625 µg oligo-dT pretreatment before reverse transcription. Oligo-dT sample 1.25 µg: HCV cDNA sample with a concentration of 5,000 copies/ml was amplified with 1.25 µg oligo-dT pretreatment before reverse transcription. Oligo-dT sample 2.5 µg: HCV cDNA sample with a concentration of 5,000 copies/ml was amplified with 2.5 µg oligo-dT pretreatment before reverse transcription. Without (w/o) oligo-dT sample: HCV cDNA sample with a concentration of 5,000 copies/ml was amplified without oligo-dT pretreatment before reverse transcription.

Observed Results:

As can be taken from FIG. 1, the specific 392 bp PCR product was generated for all HCV cDNA samples. No high molecular weight products were generated in the samples with oligo-dT pretreatment before reverse transcription (With oligo-dT: lanes 1, 2 and 3 for samples 5, 25 and 100, respectively). However, high molecular weight products were generated in the samples without oligo-dT pretreatment before reverse transcription (w/o oligo-dT: sample 25, both lanes).

Figure 2:
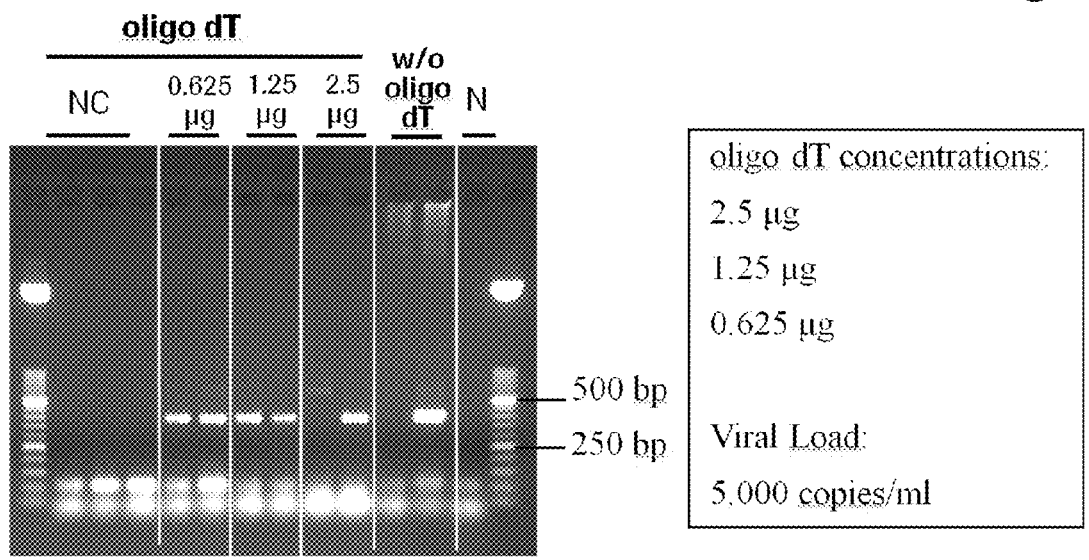
FIG. 2: The Figure shows the comparison of PCR products using an HCV specific primer set for HCV genotype 1a with and without oligo-dT pretreatment before reverse transcription. Different concentrations of oligo-dT are compared at a specific concentration of HCV cDNA.

As can be taken from FIG. 2, the specific 392 bp PCR product is present in all samples except one replicate in the 2.5 µg oligo-dT sample and one replicate in the sample w/o oligo-dT. No high molecular weight products were generated in the samples with oligo-dT pretreatment before reverse transcription (With oligo-dT: samples 0.625 µg, 1.25 µg and 2.5 µg). 0.625 µg oligo-dT is shown to prevent high molecular weight product generation completely and is defined as amount of oligo-dT to be used. In the sample w/o oligo-dT, high molecular weight products are present.

The invention claimed is:

1. A method of reverse transcription, wherein the method comprises the steps of
   a) providing a sample comprising RNA,
   b) contacting the sample with a carrier nucleic acid thereby generating a mixture, wherein the carrier nucleic acid is polyA-RNA,
   c) applying the mixture to a matrix under conditions such that binding of the RNA and the carrier nucleic acid to the matrix occurs,
   d) separating the matrix with the RNA and the carrier nucleic acid bound to the matrix from the mixture,
   e) eluting the RNA and the carrier nucleic acid from the matrix thereby generating an eluate,
   f) adding a blocking nucleic acid to the eluate under conditions such that hybridization of the blocking nucleic acid to the carrier nucleic acid occurs, wherein the blocking nucleic acid is an oligo-dT molecule modified at the 3' end to prevent extension of the oligo-dT molecule by a polymerase reaction,
   g) adding a primer to the eluate from step f) under conditions such that hybridization of the primer to the RNA occurs, and
   h) reverse transcribing the RNA into cDNA.

2. The method of claim 1, wherein the oligo-dT molecule is 5'-(dT)n-X-3', wherein (dT)n is a n-mer homo-2'-deoxythymidine oligonucleotide, wherein n is 18, 19, 20, 21 or 22, wherein X is selected from the group consisting of p, pC3, pC3p, pC3pC3 and pC3pC3p, and wherein X is bound to the 3'-terminal hydroxyl group of (dT)n and wherein p is a phosphate and C3 is a 1,3-propanediol spacer.

3. The method of claim 2, wherein n is 20 and X is pC3pC3p.

4. The method of claim 1, wherein the primer is a random primer.

5. The method of claim 4, wherein the random primer is a random hexamer primer.

6. The method of claim 1, wherein the matrix comprises a glass fiber fleece.

7. The method of claim 1, wherein the sample is selected from the group consisting of serum, blood, plasma, tears, cell culture supernatant, urine and breast milk, saliva, cerebrospinal fluid and sperm.

8. The method of claim 7, wherein the sample is plasma.

* * * * *